US00PP19894P2

(12) United States Plant Patent

Egger et al.

(10) Patent No.: US PP19,894 P2

(45) Date of Patent: Apr. 7, 2009

(54) *CYCLAMEN* PLANT NAMED 'SOMETHING MAGIC'

(50) Latin Name: *Cyclamen coum*
Varietal Denomination: Something Magic

(75) Inventors: Janet N. Egger, Wilsonville, OR (US); Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/011,827

(22) Filed: Jan. 29, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—Klarquist Sparkman, LLP

(57) ABSTRACT

A new and distinct *Cyclamen* plant characterized by large, bright pink flowers, foliage strongly silvered with a triangular green patch in the center (Christmas tree pattern), a quick bloom time (blooms in first year from tissue culture), and excellent vigor.

1 Drawing Sheet

Botanical denomination: *Cyclamen coum.*
Variety designation: 'Something Magic'.

BACKGROUND OF THE INVENTION

The present invention relates to a new and distinct cultivar of *Cyclamen coum* and given the cultivar name of 'Something Magic'. *Cyclamen* is in the family *Primulaceae.* The new cultivar originated from a planned breeding program to produce a vigorous plant with "Christmas tree" pattern on the leaf for tissue culture production. The new cultivar resulted from pollination controlled. The exact parents are unknown.

Compared to other *Cyclamen coum* on the market, this new cultivar is the first one, to the inventors' knowledge, that is multiplied in tissue culture. This has the advantage of being able to produce a uniform crop. This clone also blooms in the first year, after its natural dormancy. Seed varieties do not flower uniformly and do not flower until their second year or later.

SUMMARY OF THE INVENTION

This new *Cyclamen* is distinguished by:

1. large, bright pink flowers;
2. foliage strongly silvered with a triangular green patch in the center ("Christmas tree" pattern);
3. quick bloom time (blooms in first year from tissue culture);
4. excellent vigor.

This new cultivar has been reproduced only by asexual propagation (tissue culture). Each of the progeny exhibits identical characteristics to the original plant. Asexual propagation by tissue culture using standard micropropagation techniques with terminal shoots, as done in Canby, Oreg. shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
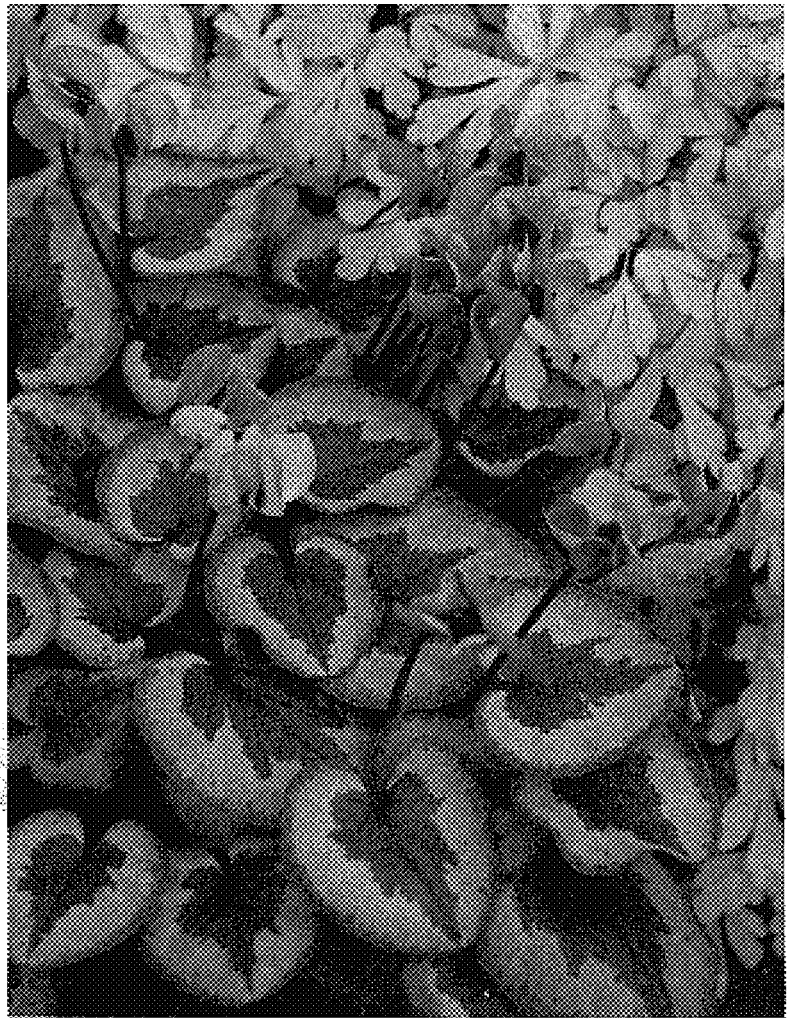
FIG. 1 shows the flowers, foliage, and habit of a 1 year old *Cyclamen* 'Something Magic' in April.
Figure 2:
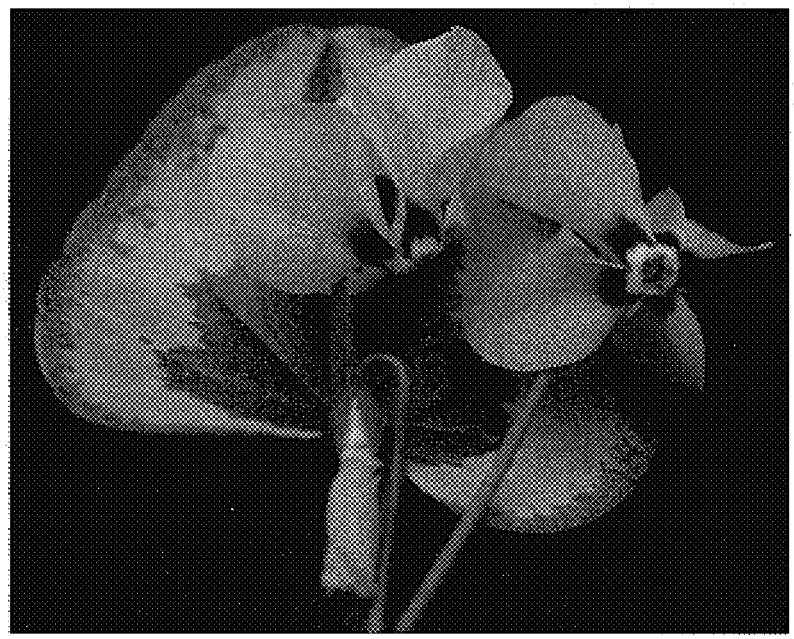
FIG. 2 shows a close up of the flowers and one leaf.

The following is a detailed description of the new *Cyclamen* based on observations of one-year-old specimens grown in 4" containers in an unheated greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on the Royal Horticultural Society Colour Chart.

Plant:

*Type.*—Tuberous herbaceous perennial.
*Hardiness.*—USDA Zones 5 to 9.
*Size.*—14 cm wide and 5 cm tall.
*Form.*—Clumping.
*Vigor.*—Excellent.
*Roots.*—From the center of the base of the tuber, fibrous, much branched.
*Tuber.*—Depressed globose, 10 mm wide and 5 mm deep, Brown 199B, surface texture smooth with velvety pubescence.

Leaf:

*Number.*—20 to 30 in number.
*Type.*—Simple.
*Shape.*—Orbicular to cordate and cup down slightly.
*Arrangement.*—Rosette.
*Blade length.*—Grows to 4 cm.
*Blade width.*—Grows to 4 cm.
*Margins.*—Entire.
*Apex.*—Obtuse to subacute.
*Base.*—Cordate.
*Venation.*—Palmate.
*Surface texture.*—Glabrous on both surfaces.
*Petiole description.*—Grows to 6.5 cm long and 1.7 mm wide, glandular, Brown 200A, not straight.

*Color.*—Topside center deep green, Green 139A (in a triangular pattern, irregularly edged) surrounded by a section 5 mm to 10 mm wide of silver, Greyed Green 194A, and with the margin edge Green 139A; bottom side is closest to Greyed Purple 187B.

Inflorescence:

*Type.*—Solitary, nodding.

*Number of flowers in first spring flush.*—10.

*Pedicel.*—Grows to 11 cm long, 1.3 mm wide, glandular, not straight, Greyed Orange 166A.

Flower Bud:

*Size.*—20 mm long and 4 mm wide.

*Shape.*—Cylindrical, downward pointing.

*Color.*—Red Purple 71B.

Flower:

*Type.*—Bisexual.

*Corolla description.*—Overall size 22 mm deep and 25 mm wide, glabrous inside and out; tube downward pointing and urseolate, 5 mm long and 5 mm wide, White 155B inside and out; lobes 5 in number, reflexed and twisted, each lobe grows to 21 mm long and 16 mm wide, obovate with a clawed base, margin on top half unevenly slightly dentate, bottom half entire, tip obtuse, main lobe color: top side Purple 78A, lightening toward base, with basal spot Greyed Purple 187A, lobe base Red Purple 65D giving a white "eye" look, backside the same except the basal spot is lighter.

*Calyx description.*—7 mm long and 5 mm wide with 5 narrow lobes each 5 mm long and 1.5 mm wide, tubular campanulate, lanceolate, entire, tips acute, glabrous, color inside and out closest to Brown 200B.

*Pistil description.*—One, 6.5 mm long, ovary globose, 1 mm deep and wide, Greyed Brown 199D, style 5.5 mm long, White 155A, stigma White 155A.

*Stamen description.*—5 in number, 4.5 mm long and 1 mm wide, attached to and inserted in the top of tube, filaments 0.5 mm long, White 155A, anthers 4.5 mm long and 1 mm wide, Yellow Orange 14B; pollen Yellow 7A.

*Bloom period.*—February to May in Canby, Oreg.

*Lastingness of bloom.*—Each flower lasts about a week.

*Fragrance.*—None.

Fruit: a subglobose capsule, 6 mm to 7 mm wide and 5 mm deep, papery when mature, Brown 200A.

Seed: usually 6 to 10 in number, Brown 200A, oval with flattened sides, 2 mm long and 1.5 mm wide.

Pest and diseases: *Cyclamen coum* are troubled by spider mites and botrytis. This variety has no known resistances.

Comparisons: Compared to other *Cyclamen coum* on the market, this new cultivar is the first one to the inventor's knowledge that is multiplied in tissue culture. This has the advantage of being able to produce a uniform crop. This clone also blooms in the first year if it has been allowed to go dormant. Seed varieties do not flower uniformly and do not flower until their second year or later.

We claim:

1. A new and distinct *Cyclamen* plant as herein illustrated and described.

* * * * *